US00PP20083P2

(12) United States Plant Patent
Spek

(10) Patent No.: US PP20,083 P2
(45) Date of Patent: Jun. 9, 2009

(54) *ILEX* PLANT NAMED 'NORTHERN LIGHTS'

(50) Latin Name: *Ilex aquifolium*
Varietal Denomination: Northern Lights

(75) Inventor: Peter Spek, Boskoop (NL)

(73) Assignee: Joh. Spek Boomkwekerijen B.V., Boskoop (NL)

( * ) Notice: Subject to any disclaimer, the term of this patent is extended or adjusted under 35 U.S.C. 154(b) by 0 days.

(21) Appl. No.: 12/011,392

(22) Filed: Jan. 25, 2008

(51) Int. Cl.
*A01H 5/00* (2006.01)

(52) U.S. Cl. ..... Plt./247
(58) Field of Classification Search ..... Plt./247
See application file for complete search history.

*Primary Examiner*—Annette H Para
(74) *Attorney, Agent, or Firm*—C. A. Whealy

(57) ABSTRACT

A new and distinct cultivar of *Ilex* plant named 'Northen Lights', characterized by its upright plant habit; freely branching habit; dark green and yellow green bi-colored foliage with sharp spines; and good garden performance.

2 Drawing Sheets

Botanical designation: *Ilex aquifolium.*
Cultivar denomination: 'Northern Lights'.

BACKGROUND OF THE INVENTION

The present Invention relates to a new and distinct cultivar of *Ilex,* botanically known as *Ilex aguifolium,* and hereinafter referred to by the name 'Northen Lights'.

The new *Ilex* is a naturally-occurring branch mutation of the *Ilex aquifolium* cultivar Alaska, not patented. The new *Ilex* was discovered and selected by the Inventor from with a population of plants of the cultivar Alaska in a controlled environment in Boskoop, The Netherlands, during the summer of 1998.

Asexual reproduction of the new *Ilex* by softwood cuttings taken in a controlled environment in Boskoop, The Netherlands since the summer of 1998 has shown that the unique features of this new *Ilex* are stable and reproduced true to type in successive generations.

SUMMARY OF THE INVENTION

The new *Ilex* has not been observed under all possible environmental conditions. The phenotype may vary somewhat with variations in environment such as temperature and/or light intensity without, however, any variance in genotype. The following traits have been repeatedly observed and are determined to be the unique characteristics of 'Northen Lights'. These characteristics in combination distinguish 'Northen Lights' as a new and distinct cultivar of *Ilex:*

1. Upright plant habit.
2. Freely branching habit.
3. Dark green and yellow green bi-colored foliage with sharp spines.
4. Good garden performance.

Plants of the new *Ilex* differ from plants of the parent, the cultivar Alaska, primarily in foliage color as plants of the cultivar Alaska have dark green-colored foliage.

Plants of the new *Ilex* can be compared to the plants of the *Ilex aquifolium* cultivar Silver Milkboy, not patented. In side-by-side comparisons conducted in Boskoop, The Netherlands, plants of the new *Ilex* differed from plants of the cultivar Silver Milkboy in the following characteristics:

1. Plants of the new *Ilex* were more upright and uniform than and not as spreading as plants of the cultivar Silver Milkboy.
2. Plants of the new *Ilex* had slightly undulate leaves whereas plants of the cultivar Silver Milkboy had strongly undulate leaves.

Plants of the new *Ilex* can also be compared to the plants of the *Ilex aquifolium* cultivar Maderensis Variegata, not patented. In side-by-side comparisons conducted in Boskoop, The Netherlands, plants of the new *Ilex* differed from plants of the cultivar Maderensis Variegata in the following characteristics:

1. Plants of the new *Ilex* were more upright and uniform than and not as spreading as plants of the cultivar Maderensis Variegata.
2. Plants of the new *Ilex* had spinose leaves whereas plants of the cultivar Maderensis Variegata had entire leaves.

BRIEF DESCRIPTION OF THE PHOTOGRAPHS

The accompanying colored photographs illustrate the overall appearance of the new *Ilex.* These photographs show the colors as true as it is reasonably possible to obtain in colored reproductions of this type. Colors in the photographs may differ slightly from the color values cited in the detailed botanical description, which accurately describe the colors of the new *Ilex.*

The photograph on the first sheet comprises a side perspective view of typical plants of 'Northen Lights' grown in an outdoor nursery.

The photograph on the second sheet is a close-up view of a typical leaf of 'Northen Lights'.

DETAILED BOTANICAL DESCRIPTION

The aforementioned photographs and following observations and measurements describe plants grown in Boskoop, The Netherlands in 19-cm containers, in an outdoor nursery during the autumn and under commercial production conditions. During the production of the plants, day temperatures ranged from 9° C. to 18° C. and night temperatures ranged from 1° C. to 10° C. Plants used for the photographs and description were about five years old. In the following description, color references are made to The Royal Horticultural Society Colour Chart, 2001 Edition, except where general terms of ordinary dictionary significance are used.

Botanical classification: *Ilex aquifolium* 'Northen Lights'.

Parentage: Naturally-occurring branch mutation of the *Ilex aguifolium* cultivar Alaska, not patented.

Propagation:

*Type.*—By softwood cuttings.

*Time to initiate roots, summer.*—About 45 days at temperatures of 25° C.

*Time to produce a rooted young plant, summer.*—About four months at temperatures of 25° C.

*Root description.*—Medium in thickness, moderately fleshy; light greyish brown in color.

*Rooting habit.*—Moderate branching; moderately dense.

Plant description:

*Plant form and growth habit.*—Perennial evergreen shrub; upright plant habit; inverted triangle. Moderately vigorous growth habit.

*Branching habit.*—Freely branching habit; one primary lateral branches and about 52 secondary lateral branches developing per plant.

*Plant height.*—About 1.76 meters.

*Plant diameter, area of spread.*—About 85 cm.

*Lateral branch description.*—Length: About 38 cm. Diameter: About 4.5 mm. Internode length: About 1.2 cm. Strength: Very strong. Texture: Smooth, glabrous. Color, young stems: 137B to 137C; axial stripes, N144A. Color, mature stems: 137A; axial stripes, N144A to N144B.

*Foliage description.*—Arrangement: Alternate, simple. Length: About 5.4 cm. Width: About 2.9 cm. Shape: Ovate. Apex: Sharply apiculate. Base: Attenuate. Margin: Spinose, about 13 spines on each side. Venation pattern: Pinnate. Texture, upper and lower surfaces: Smooth, glabrous; thick and leathery.

*Color.*—Developing foliage, upper surface: Central blotch, N144A; margins, between 143A and 144A. Developing foliage, lower surface: 144B to 144C. Fully expanded foliage, upper surface: Central blotch, between 4A and 5B to 5C; margins, much darker than 139A with lighter spots, between 143A and 144A; venation, similar to lamina; spines, 148A to 148B. Fully expanded foliage, lower surface: Central blotch, N144A to N144B; margins, 137C; venation, between 8C and 11B.

*Petiole.*—About 8 mm. Diameter: About 2 mm. Texture, upper and lower surfaces: Smooth, glabrous. Color, upper and lower surfaces: 144A to 144B.

Flower description:

A description of the flowers is not available to date as flower development has not been observed on plants of the new *Ilex*.

Garden performance: Plants of the new *Ilex* have been observed to have good garden performance and to be tolerant to rain and wind. Plants of the new *Ilex* are hardy to USDA Zone 6 and tolerate high temperatures up to 35° C.

Disease/pest resistance: Plants have not been observed to be resistant to pathogens and pests common to *Ilex*.

It is claimed:

1. A new and distinct cultivar of *Ilex* plant named 'Northen Lights' as illustrated and described.

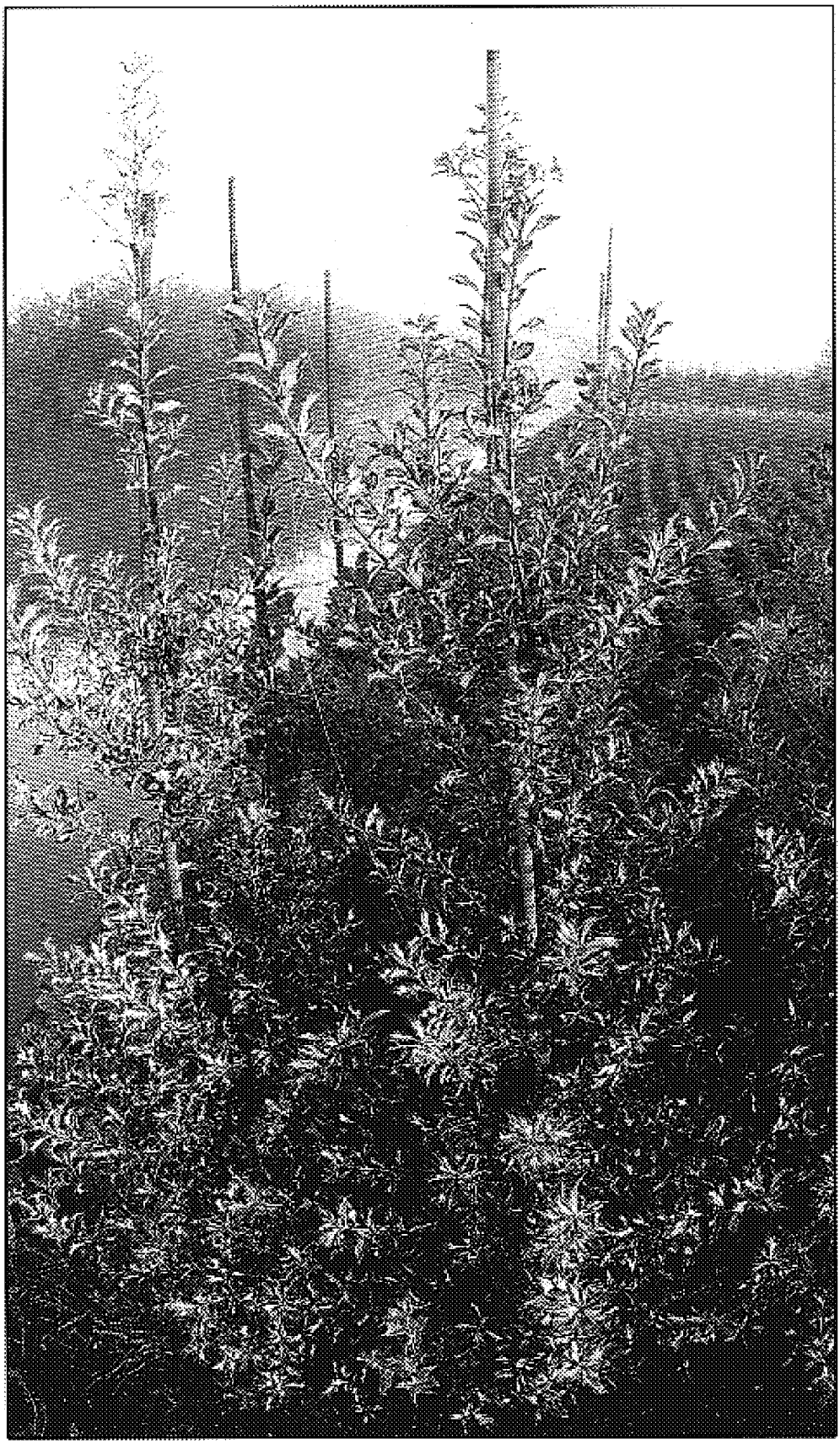

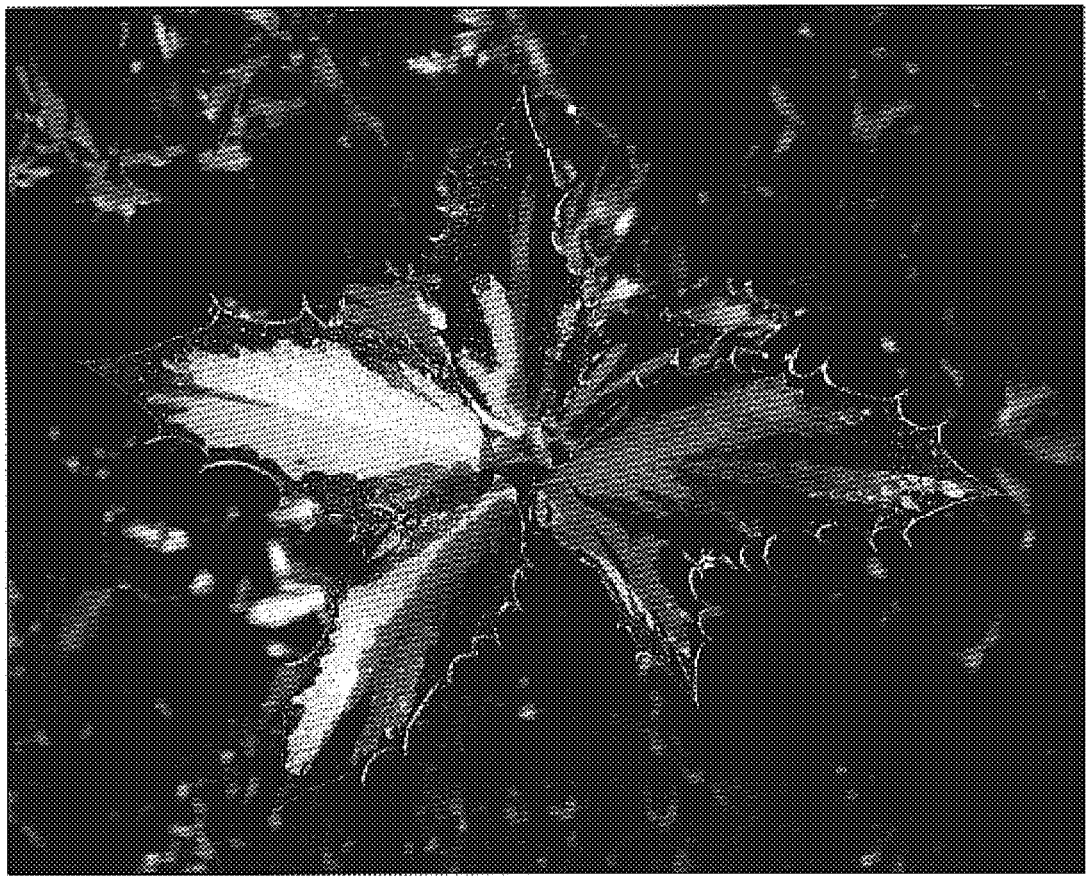

* * * * *